(12) United States Patent
Kreischer

(10) Patent No.: US 7,476,775 B2
(45) Date of Patent: Jan. 13, 2009

(54) METHOD AND SYSTEM FOR SEPARATING AN OLIGOMERIZATION REACTOR EFFLUENT

(75) Inventor: Bruce E. Kreischer, Humble, TX (US)

(73) Assignee: Chevron Phillips Chemical Company LP, The Woodlands, TX (US)

(*) Notice: Subject to any disclaimer, the term of this patent is extended or adjusted under 35 U.S.C. 154(b) by 979 days.

(21) Appl. No.: 10/792,108

(22) Filed: Mar. 3, 2004

(65) Prior Publication Data

US 2005/0197521 A1 Sep. 8, 2005

(51) Int. Cl.
*C07C 7/00* (2006.01)
*C07C 2/24* (2006.01)
*B01D 3/00* (2006.01)

(52) U.S. Cl. .................. 585/809; 202/152; 585/512

(58) Field of Classification Search .......... 202/152, 202/154, 156; 585/512, 809
See application file for complete search history.

(56) References Cited

U.S. PATENT DOCUMENTS

| | | |
|---|---|---|
| 3,418,215 A | 12/1968 | Nirenberg |
| 5,689,028 A | 11/1997 | Lashier et al. .............. 585/512 |
| 5,750,816 A | 5/1998 | Araki et al. ................. 585/512 |

FOREIGN PATENT DOCUMENTS

| | | |
|---|---|---|
| WO | WO 99/19280 | 4/1999 |
| WO | WO 9919280 A1 * | 4/1999 |
| WO | WO 03/053890 A1 | 7/2003 |
| WO | WO 03053890 A1 * | 7/2003 |

OTHER PUBLICATIONS

Perry's Chemical Engineers' Handbook, 7th ed. New York, McGraw Hill, 1997, pp. 13-4-13-9.*
Written Opinion and International Search Report of PCT/US2005/006732 dated Jul. 29, 2005, 7 pages.

* cited by examiner

*Primary Examiner*—Glenn Caldarola
*Assistant Examiner*—Randy Boyer
(74) *Attorney, Agent, or Firm*—Conley Rose, P.C.; Rodney B. Carroll; Stephen R. Jenkins

(57) ABSTRACT

A method of separating an oligomerization reactor effluent, comprising: flashing the oligomerization reactor effluent into a liquid portion and a vapor portion, distilling the liquid and the vapor portions of the oligomerization reactor effluent and recovering an oligomerization product stream. A system for separating an oligomerization reactor effluent comprising liquid and vapor portions: a vapor/liquid separator to flash the oligomerization reactor effluent into a vapor portion and a liquid portion, and a distillation column in fluid communication with the vapor/liquid separator, wherein the distillation column has a side draw for withdrawing an oligomerization product stream and receives as separate feeds the vapor portion and the liquid portion from the vapor/liquid separator.

30 Claims, 1 Drawing Sheet

METHOD AND SYSTEM FOR SEPARATING AN OLIGOMERIZATION REACTOR EFFLUENT

CROSS-REFERENCE TO RELATED APPLICATIONS

Not Applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

The present invention generally relates to olefin production. More specifically, the invention relates to methods and systems for separating an oligomerization reactor effluent comprising compounds such as ethylene and 1-hexene.

BACKGROUND OF THE INVENTION

In the field of olefin production, a process to selectively produce high purity 1-hexene from the trimerization of ethylene involves the separation of an oligomerization reactor effluent into four major streams: product, unconverted ethylene, recovered solvent, and heavies. Typically the separation of the oligomerization reactor effluent to obtain high purity 1-hexene can be achieved with three distillation steps operated in series, wherein the first distillation column separates the ethylene from the remaining constituents in the bottoms that then becomes the feed for a second column, wherein the product is stripped off and a distillate of high purity 1-hexene is obtained. The bottoms become the feed for a third distillation column, wherein the heavies/solvent split is made. Multiple separation steps such as these involving distillation columns can be costly. Therefore, a need exists for process improvements to separate oligomerization reactor effluent.

SUMMARY OF THE INVENTION

Disclosed herein is a method of separating an oligomerization reactor effluent, comprising: (a) flashing the oligomerization reactor effluent into a vapor portion and a liquid portion; (b) distilling the portions of the oligomerization reactor effluent; and (c) recovering an oligomerization product stream.

Further disclosed herein is a method of separating an oligomerization reactor effluent, comprising: (a) feeding a liquid portion of the oligomerization reactor effluent to a first inlet on a distillation column; (b) feeding a vapor portion of the oligomerization reactor effluent to a second inlet on a distillation column located above the first inlet; and (c) withdrawing an oligomerization product stream from a side drawn outlet located between the first and second inlets.

Further disclosed herein is a system for separating an oligomerization reactor effluent comprising: (a) a vapor/liquid separator to flash the oligomerization reactor effluent into a Vapor portion and a liquid portion; and (b) a distillation column in fluid communication with the vapor/liquid separator, wherein the distillation column has a side draw for withdrawing an oligomerization product stream and receives as feed the vapor portion and the liquid portion from the vapor/liquid separator.

DETAILED DESCRIPTION OF THE PREFERRED EMBODIMENTS

Figure 1:
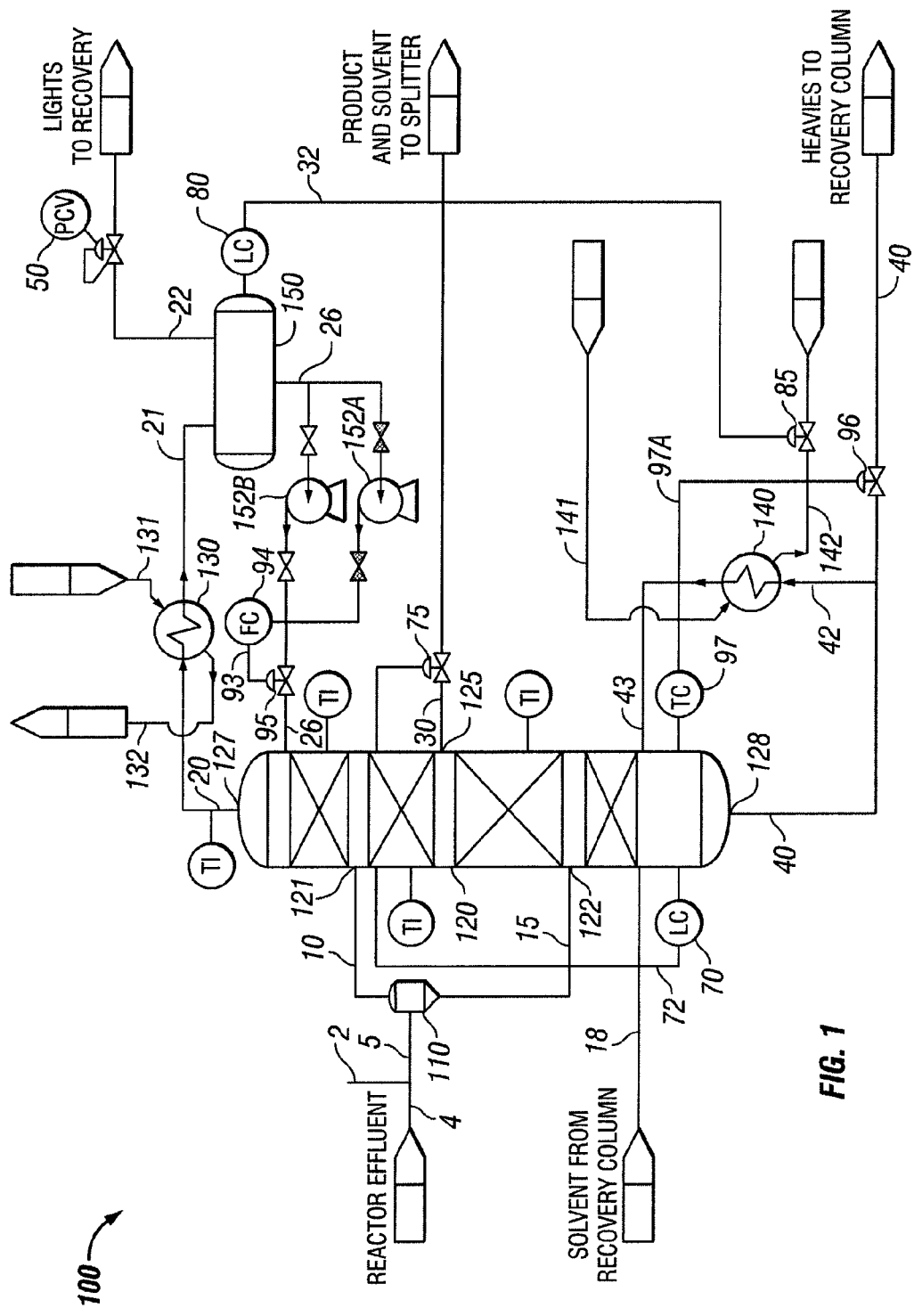
FIG. 1 is a process flow diagram of an embodiment of a system to separate components of an oligomerization reactor effluent stream.

FIG. 1 shows a process flow diagram for an embodiment of a separation system 100 to separate oligomerization reactor effluent, the separation system comprising a vapor/liquid separator 110 to flash the oligomerization reactor effluent into a vapor portion and a liquid portion, and a distillation column 120 in fluid communication with the vapor/liquid separator 110. The distillation column 120 has a side draw outlet 125 for withdrawing the oligomerization product stream and depending on the solvent used, possibly solvent, and receives as feed the separated vapor portion and liquid portion from the vapor/liquid separator 110. The liquid portion is fed to the distillation column 120 at a location, liquid feed inlet 122, below the side draw outlet 125 and the vapor portion is fed to the distillation column 120 at a location, vapor feed inlet 121, above the side draw outlet 125. The separation system 100 further comprises an oligomerization reactor (not shown) for providing the oligomerization reactor effluent, wherein the oligomerization reactor is in fluid communication with the vapor/liquid separator 110.

In FIG. 1, oligomerization reactor effluent is introduced to the vapor/liquid separator 110 via reactor effluent stream 4. Any suitable oligomerization reaction can provide the oligomerization reaction products found in reactor effluent stream 4 of FIG. 1. In a embodiment, the oligomerization reaction is a trimerization reaction of ethylene to 1-hexene, for example according to the method and apparatus disclosed in International Publication Number WO 99/19280, entitled "Process for the Trimerization of Olefins", filed on Jul. 17, 1998, incorporated by reference herein in its entirety. The remainder of the detailed description focuses primarily on such an embodiment wherein 1-hexene is recovered from the effluent of an ethylene trimerization reactor, but it should be understood that the scope of the present invention is defined by the claims and not limited to a particular embodiment described herein.

Trimerization, as used herein, is defined as the combination of three olefins, wherein the number of olefins, i.e., carbon-carbon double bonds, is reduced by two. Reactants applicable for use in the trimerization process of this disclosure are olefinic compounds which can self react, i.e., trimerize, to give useful products such as, for example, the self reaction of ethylene to give 1-hexene. Additionally, ethylene trimerization may result in a higher yield of 1-hexene with a desirable purity when trimerized in the presence of a chromium-based catalyst system.

As used in this disclosure, "reactor effluent" refers to all components that can be present in and can be removed from an oligomerization reactor, including, but not limited to, trimerization product(s) such as 1-hexene, unreacted olefin such as ethylene, solvent, catalyst system components, catalyst system residues, and/or reaction co-product(s), also referred to as reaction by-product(s) included in lights and heavies. "Solvent" refers to a diluent or medium, such as an aliphatic solvent, an aromatic solvent, or combinations thereof, having from about 3 to 9 carbon atoms, in which the trimerization process occurs. Exemplary solvents include, but are not limited to, cyclohexane, methylcyclohexane, hexane, 1-hexene, $C_7$ hydrocarbons (e.g., n-heptane), isobutane, propane, toluene, xylenes, ortho-xylene, meta-xylene, para-xylene, ethylbenzene, and mixtures of two or more thereof. Isobutane can be used for enhanced compatibility with known olefin polymerization processes. However, a homogenous trimerization catalyst system may be more soluble in cyclohexane. In an embodiment, the solvent is cyclohexane.

In addition to olefin feed, hydrogen can be optionally fed into the trimerization reactor to accelerate the reaction and/or increase catalyst system activity and may also be an unreacted component in the reactor effluent. "Lights" refers to reaction co-product(s) comprising hydrocarbon compounds having less than about 5 carbon atoms per molecule, excluding ethylene, and including other non-hydrocarbon compounds including hydrogen, nitrogen, oxygen, carbon monoxide, carbon dioxide, and water. "Heavies" refers to reaction co-product(s) comprising hydrocarbon compounds having from about 7 to about 100 carbon atoms per molecule, excluding solvent. Heavies may also include higher olefinic products, such as, for example decenes and tetradecenes, as well as polymeric products, catalyst, deactivated catalyst, and catalyst kill agent.

In an embodiment, catalyst system deactivation, i.e., "kill", components, can be fed via inlet stream 2 into reactor effluent stream 5. "Catalyst kill" refers to those compounds that can deactivate, either partially or completely, a catalyst system used in the trimerization process. In an embodiment, the catalyst system may be killed with an amine, an alcohol having from eight to twelve carbon atoms per molecule, or combinations thereof. In an embodiment, the kill component is $C_8$ alcohol. In an embodiment, the $C_8$ alcohol is 2-ethyl-1-hexanol. The catalyst system may be deactivated according to the method and apparatus in the U.S. Pat. No. 5,689,028, entitled "Process to Regulate Olefin Production by Catalyst System Inhibition", filed on Dec. 18, 1995, incorporated by reference herein in its entirety. In such an embodiment, reactor effluent stream 5 would additionally comprise kill component along with other components previously mentioned before being introduced into vapor/liquid separator 110.

In an embodiment, the reactor effluent stream 4 may comprise: from about 5 to about 60 wt. % 1-hexene, alternatively from about 10 to about 40 wt. % 1-hexene, and alternatively from about 15 to about 30 wt. % 1-hexene; from about 1 to about 30 wt. % ethylene, alternatively from about 3 to about 20 wt. % ethylene, and alternatively from about 5 to about 15 wt. % ethylene; from about 15 to about 95 wt. % cyclohexane (solvent), alternatively from about 30 to about 85 wt. % cyclohexane, and alternatively from about 50 to about 80 wt. % cyclohexane; from about 1 to about 40 wt. % lights, alternatively from about 3 to about 30 wt. % lights, and alternatively from about 5 to about 20 wt. % lights; and from about less than 15 wt. % heavies, alternatively from less than about 10 wt. % heavies, and alternatively from about 0 to about 3 wt. % heavies. In an embodiment, the reactor effluent stream 4 may be at a pressure of about 650 to about 1000 psig and a temperature of about 220 to about 260° F.

In FIG. 1, the reactor effluent is introduced into the vapor/liquid separator 110 via reactor effluent stream 5 where the pressure is reduced and at least a portion of reactor effluent may be flashed to a vapor portion. Vapor/liquid separator 110 used for separating the reactor effluent into a vapor portion and a liquid portion should be designed in such a way as to minimize liquid carry-over with the vapor stream and minimize liquid holdup within the separator itself. The liquid portion is removed from the bottom of the vapor/liquid separator 110 and fed into the distillation column 120 via stream 15. The vapor portion is removed from the top of vapor/liquid separator 110 and fed into distillation column 120 via stream 10. In an embodiment, elevation of the vapor/liquid separator 110 to a location that is above the liquid feed inlet 122 to distillation column 120, can provide a resultant hydraulic head and/or gravity that will enable the liquid portion to flow into the distillation column 120. Alternatively, if the separator is located at grade or other location that is below the liquid feed inlet 122, a pump may be used to pump the liquid portion into distillation column 120.

In an embodiment, the liquid portion of the separated reactor effluent product in stream 15 may comprise: from about 5 to about 60 wt. % 1-hexene, alternatively from about 10 to about 40 wt. % 1-hexene, and alternatively from about 15 to about 30 wt. % 1-hexene; from about 1 to about 15 wt. % ethylene, alternatively from about 3 to about 10 wt. % ethylene, and alternatively from about 0 to about 5 wt. % ethylene; from about 25 to about 90 wt. % cyclohexane (solvent), alternatively from about 40 to about 85 wt. % cyclohexane, and alternatively from about 50 to about 80 wt. % cyclohexane; from about 1 to about 15 wt. % lights, alternatively from about 3 to about 10 wt. % lights, and alternatively from about 0 to about 5 wt. % lights; and from 1 to about 15 wt. % heavies, alternatively from about 3 to about 10 wt. % heavies, and alternatively from about 0 to about 5 wt. % heavies. In an embodiment, stream 15 may be at a pressure of about 85 to about 115 psig and a temperature of about 200 to about 260° F.

Additionally, the vapor portion of the separated reactor effluent in stream 10 may comprise: from about 5 to about 50 wt. % 1-hexene, alternatively from about 10 to about 40 wt. % 1-hexene, and alternatively from about 15 to about 25 wt. % 1-hexene; from about 10 to about 80 wt. % ethylene, alternatively from about 20 to about 60 wt. % ethylene, and alternatively from about 25 to about 50 wt. % ethylene; from about 5 to about 70 wt. % cyclohexane (solvent), alternatively from about 10 to about 50 wt. % cyclohexane, and alternatively from about 20 to about 40 wt. % cyclohexane; from about 15 to about 80 wt. % lights, alternatively from about 20 to about 60 wt. % lights, and alternatively from about 25 to about 50 wt. % lights; and from about 0 to about 5 wt. % heavies, alternatively from about 0 to about 2 wt. % heavies, and alternatively from about 0 to about 0.5 wt. % heavies. In an embodiment, stream 10 may be at a pressure of about 85 to about 115 psig and a temperature of about 200 to about 260° F.

The distillation column 120 may be a continuous distillation column with separation stages comprised of trays (not shown), packing material (as shown in FIG. 1), or a combination of both. In an embodiment, the distillation column 120 may have at least 3 off-takes and at least 2 inputs. For example, in FIG. 1, distillation column 120 has 3 off-takes and 2 inputs. The off-takes include an oligomerization product stream 30 from side draw outlet 125 comprising oligomerization product (e.g., 1-hexene) and possibly solvent (e.g., cyclohexane); an overhead vapor stream 20 comprising unreacted olefin (e.g., ethylene) and lights; and a bottoms stream 40 comprising heavies. The solvent may exit distillation column 120 in any of the three off-take streams, depending on the solvent used, for example, in an embodiment cyclohexane is the solvent and exits distillation column 120 in the oligomerization product stream 30 from side draw outlet 125.

The 2 inputs to distillation column 120 comprise a vapor feed from stream 10 and a liquid feed from stream 15 from vapor/liquid separator 110 which enter in the vapor feed inlet 121 and the liquid feed inlet 122, respectively, the compositions of each as described herein. The solvent may enter the distillation column 120 through any of the two input streams, stream 10, stream 15, or both, depending upon the solvent used and the completeness of separation (e.g., solvent flash) in vapor/liquid separator 110. In an embodiment, the flashes and separations may not be complete and at least a portion of the vapor portion enters at the liquid feed inlet and/or vice-versa. In an embodiment, a first portion of solvent may enter in the vapor feed inlet 121 and a second portion of the solvent may enter in the liquid feed inlet 122, the first portion of solvent being much greater than the second portion of solvent; alternatively a first portion of solvent may enter in the vapor feed inlet 121 and a second portion of the solvent may enter in the liquid feed inlet 122, the second portion of solvent being much greater than the first portion of solvent; or alternatively a first portion of solvent may enter in the vapor feed inlet 121 and a second portion of the solvent may enter in the liquid feed inlet 122, the first portion of solvent being slightly greater than, slightly less than, or about equal to the second portion of solvent. In an embodiment, equal to or greater than about 90 weight percent of the solvent is contained in either the vapor feed from stream 10 or the liquid feed from stream 15; alternatively equal to or greater than 95 weight percent; alternatively equal to or greater than about 99 weight percent; alternatively equal to or greater than about 99.9 weight percent; where the remainder of the solvent is in the other stream. For example, in an embodiment the solvent is cyclohexane, the majority of which enters the distillation column via liquid stream 15 at liquid feed inlet 122 and exits the distillation column primarily via side draw outlet 125. In an embodiment, the solvent is isobutane, the majority of which enters the distillation column via vapor feed stream 10 at vapor feed inlet 121 and exits the distillation column primarily via side draw outlet 125.

In FIG. 1, the product (e.g., 1-hexene) or product/solvent (e.g., 1-hexene and cyclohexane) mixture may be withdrawn from the side draw outlet 125 located between a vapor feed inlet 121 and a liquid feed inlet 122 on the distillation column. Embodiments for optimum locations of vapor feed inlet 121 and liquid feed inlet 122 on the distillation column depend on the stream compositions (including solvent used) and operating conditions. Placement of the vapor and liquid inlets is such that a number of stages is employed between the liquid feed inlet 122 (below) and the side draw outlet 125 (above) effective to separate the heavies from the product or product/solvent and a number of stages is employed between the vapor feed inlet 121 (above) and the side draw outlet 125 (below) effective to separate the lights from the product or product/solvent. In an embodiment, the liquid feed inlet 122 is located in a lower stripping section of the column and the vapor feed inlet 121 is located in an upper enriching section of the column.

For given operating conditions, process simulations may be run to determine optimum locations for the two feed inlets 121 and 122, optimum location for the side draw outlet 125 and optimum number and position of stages. For example, in an embodiment, a distillation column with 20 stages (condenser is stage 1) may be designed to have the side draw outlet 125 on stage 6, the vapor feed 121 on stage 4, and the liquid feed 122 on stage 12. In an embodiment using cyclohexane as solvent the distillation column 120 operates at overhead pressures ranging from about 85 to about 115 psig and temperatures ranging from about 100° F. at the top to about 400° F. at the bottom. The distillation column 120, vapor/liquid separator 110, and all other equipment as described herein for the separation system 100 of this disclosure may be sized to accommodate desired capacity and flow rates.

The similarities and/or differences in boiling points of each of the reactor effluent components may contribute to the ability to have a side draw off-take, as such. In an embodiment, the oligomerization product stream comprises a solvent of cyclohexane and a product of 1-hexene. The product and solvent, each of which are $C_6$'s, have boiling points that are relatively close to each other, whereas the lights and heavies may have boiling points that are relatively far apart, thereby contributing to the ability to have a side draw to separate out product/solvent (e.g., 1-hexene/cyclohexane) from the distillate (e.g., primarily ethylene and lights) and bottoms (e.g., heavies).

In an embodiment, the oligomerization product stream 30 from the side draw outlet 125 is a liquid and comprises: from about 5 to about 60 wt. % 1-hexene (product), alternatively from about 10 to about 40 wt. % 1-hexene, and alternatively from about 15 to about 30 wt. % 1-hexene; from about 0 to about 5 wt. % ethylene, alternatively from about 0 to about 2 wt. % ethylene, and alternatively from about 0 to about 0.1 wt. % ethylene; from about 40 to about 95 wt. % cyclohexane (solvent), alternatively from about 60 to about 90 wt. % cyclohexane, and alternatively from about 70 to about 85 wt. % cyclohexane; from about 0 to about 5 wt. % lights, alternatively from about 0 to about 2 wt. % lights, and alternatively from about 0 to about 0.1 wt. % lights; and from about 0 to about 5 wt. % heavies, alternatively from about 0 to about 2 wt. % heavies, and alternatively from about 0 to about 1 wt. % heavies. Stream 30 may be at a pressure of about 80 to about 120 psig and a temperature of about 275 to about 350° F.

In FIG. 1, the oligomerization product stream is withdrawn from the distillation column 120 at the side draw outlet 125, as already mentioned, and may be sent via stream 30, the flow of which is controlled by valve 75, to a splitter (not shown) for further processing to separate the oligomer product (e.g., 1-hexene) from the solvent (e.g., cyclohexane). Any suitable means for separation may be used, for example a distillation column.

The overhead vapor stream 20 exits the top of distillation column 120 through outlet 127 and may be partially condensed by a cool liquid with condenser 130. Any suitable source for cooling may be used to condense stream 20. In an embodiment, cold water from a cooling tower supply (not shown) enters the condenser 130 via stream 131, cooling the overhead vapor in stream 20 from a temperature of about 200 to about 300° F. to a temperature of about 80 to about 120° F. Condensed overheads then exit the condenser 130 via stream 21. The warmed water is returned to the cooling tower to be re-cooled via stream 132.

The condensed overhead vapor flows though stream 21 and is collected in reflux drum 150. At least a portion of the condensed overhead vapor being held in reflux drum 150 may be recycled back to the distillation column 120 for enriching the vapor stream moving upward in the column and to help maintain liquid flow downward in the distillation column 120. The recycled liquid (reflux) may be introduced into the distillation column 120 via stream 26, the flow of which is controlled by flow controller 94, control line 93, and valve 95. Reflux pump 152A and back-up pump 152B supply flow of reflux in stream 26 from reflux drum 150 to the distillation column 120. Levels in the reflux drum are controlled with level controller 80, control line 82, and valve 85 located in condensate stream 142 exiting the reboiler (to be described below). Vapor distillate is removed from reflux drum 150 via stream 22, the flow of which is controlled by valve 50. In an embodiment, the vapor distillate is primarily ethylene and can be sent via stream 22 to a compressor (not shown) and recycled back as feed to the trimerization reactor. In an embodiment, the distillate in stream 22 comprises: from about 1 to about 40 wt. % 1-hexene (product), alternatively from about 3 to about 30 wt. % 1-hexene (product), and alternatively from about 5 to about 20 wt. % 1-hexene (product); from about 35 to about 95 wt. % ethylene, alternatively from about 60 to about 92 wt. % ethylene, and alternatively from about 70 to about 90 wt. % ethylene; from about 0 to about 20 wt. % cyclohexane (solvent), alternatively from about 0 to about 15 wt. % cyclohexane, and alternatively from about 0 to about 10 wt. % cyclohexane; from about 40 to about 98 wt. % lights, alternatively from about 60 to about 96 wt. % lights, and alternatively from about 70 to about 95 wt. % lights; from about 0 to about 5 wt. % heavies, alternatively from about 0 to about 2 wt. % heavies, and alternatively from about 0 to about 0.1 wt. % heavies. In an embodiment, stream 22 may be at a pressure of about 85 to about 115 psig and a temperature of about 80 to about 120° F.

Bottoms are removed from the base of the distillation column 120 through outlet 128 and into stream 40. At least a portion of the bottoms can be returned to the lower section of the distillation column 120 via streams 42 and 43 for stripping. The bottom draw and reboiler draw may be combined (as shown) or separate (not shown). Thermal energy may be added to the returned bottoms in stream 42 by reboiler 140. Reboiler 140 may be supplied with steam or other heat source, such as a natural gas stream from a refinery or an output stream from some other distillation column, through stream 141. The reboiler 140 partially vaporizes the bottoms in stream 42 by heating it from a temperature range of about 350 to about 390° F. to a temperature range of about 355 to about 395° F. in stream 43. A vapor/liquid stream exits reboiler 140 and is returned to the distillation column via stream 43. Condensate exits reboiler 140 via stream 142.

The bottoms in stream 40 comprises: from about 0 to about 10 wt. % 1-hexene, alternatively from about 0 to about 5 wt. % 1-hexene, and alternatively from about 0 to about 3 wt. % 1-hexene; from about 0 to about 5 wt. % ethylene, alternatively from about 0 to about 2 wt. % ethylene, and alternatively from about 0 to about 0.1 wt. % ethylene; from about 20 to about 90 wt. % cyclohexane (solvent), alternatively from about 30 to about 80 wt. % cyclohexane, and alternatively from about 50 to about 75 wt. % cyclohexane; from about 0 to about 5 wt. % lights, alternatively from about 0 to about 2 wt. % lights, and alternatively from about 0 to about 0.1 wt. % lights; and from about 5 to about 70 wt. % heavies, alternatively from about 10 to about 50 wt. % heavies, and alternatively from about 15 to about 40 wt. % heavies. In an embodiment, stream 40 may be at a pressure of about 87 to about 117 psig and a temperature of about 350 to about 390° F.

The bottoms (comprised primarily of heavies) may be sent via stream 40, the flow of which is controlled with valve 96, flow controller 97, and control line 97A to a recovery distillation column (not shown) to recover solvent remaining in the bottoms stream. In addition, the recovery distillation column can be used to isolate spent catalyst, polymeric products, and/or other valued heavies, such as decenes and tetradecenes. Spent catalyst may be temperature sensitive and can decompose at temperatures higher than about 390° F.; therefore, maintaining a bottoms stream temperature below the catalyst system decomposition temperature may be desirable. In an embodiment, by recovering solvent from side draw 125, the temperature of the bottoms in stream 40 may be maintained lower than if the bottoms were concentrated to a point sufficient to recover solvent therefrom. In an embodiment, flow control of the bottoms stream may be used to aid in controlling the bottoms temperature allowing for easier control of distillation column 120, while maintaining a rate at which the recovery distillation column is capable of sufficiently processing the heavies. The recovered solvent may contain a small amount of 1-hexene and can be returned via stream 18 to the front of the separation system 100 for its subsequent recovery. Stream 18 can be introduced into the front of the separation system 100 either by directly connecting into the distillation column 120, as shown, or alternatively by connecting into stream 5 or stream 15 (not shown).

Traditionally, separation of oligomerization reactor effluent may be obtained after four distillation steps. However, the split of components following the first two of these distillation steps, typically requiring two distillation columns, can be achieved in a single distillation column by introducing a vapor/liquid separator to separate the reactor effluent into a liquid and vapor feed to the first distillation column, thus improving overall economics of the separation process. The present disclosure as described herein details such a system and method to separate oligomerization reactor effluent with a reduced number of distillation columns to a desired purity of a valued product, such as 1-hexene.

EXAMPLES

The separation system and method having been generally described, the following example is given as a particular embodiment of the separation process disclosed and to demonstrate the practice and advantages thereof. It is understood that the example given by way of illustration is not intended to limit the specification or the claims to follow in any manner.

Example 1

An embodiment of the present disclosure corresponding substantially to FIG. 1 was operated as described herein. Specifically, effluent from a trimerization reactor for the trimerization of ethylene to 1-hexene in a cyclohexane solvent was separated. Table 1 below lists operating temperatures, pressures, and stream compositions for the various numbered streams within the separation system corresponding to those numbered in FIG. 1.

TABLE 1

| | | | 5 | 15 | 10 | | | 18 | 30 | 26 | 20 |
| | | 4 | Reactor Effluent and | Distillation Column 120 | Distillation Column 120 | | | Recovered Solvent | Distillation Column | Distillation Column | Distillation Column |
| Stream Name | | Reactor Effluent | Catalyst Kill | Liquid Feed | Vapor Feed | 22 Distillate | 40 Bottoms | from Bottoms | 120 Sidedraw | 120 Reflux | 120 Overhead Vapor |
|---|---|---|---|---|---|---|---|---|---|---|---|
| 1-Hexene | wt. % | 21.78 | 21.77 | 22.60 | 18.74 | 13.46 | 1.64 | 2.22 | 24.22 | 59.49 | 52.26 |
| Ethylene | wt. % | 9.52 | 9.52 | 1.38 | 39.26 | 71.84 | 0.00 | 0.00 | 0.05 | 2.83 | 13.66 |
| Solvent | wt. % | 65.38 | 65.36 | 73.18 | 36.80 | 4.72 | 69.05 | 92.50 | 75.04 | 35.62 | 30.77 |
| Lights | wt. % | 1.27 | 1.28 | 0.33 | 4.77 | 9.86 | 0.00 | 0.00 | 0.03 | 1.44 | 2.76 |

TABLE 1-continued

| | | 4 Reactor Effluent | 5 Reactor Effluent and Catalyst Kill | 15 Distillation Column 120 Liquid Feed | 10 Distillation Column 120 Vapor Feed | 22 Distillate | 40 Bottoms | 18 Recovered Solvent from Bottoms | 30 Distillation Column 120 Sidedraw | 26 Distillation Column 120 Reflux | 20 Distillation Column 120 Overhead Vapor |
|---|---|---|---|---|---|---|---|---|---|---|---|
| Stream Name | | | | | | | | | | | |
| Heavies | wt. % | 2.04 | 2.07 | 2.52 | 0.43 | 0.12 | 29.31 | 5.28 | 0.65 | 0.61 | 0.54 |
| Temperature | F. | 260.0 | 260.0 | 219.7 | 219.7 | 115.0 | 350.0 | 196.4 | 314.8 | 115.0 | 261.8 |
| Pressure | psi | 664.7 | 664.7 | 119.7 | 119.7 | 109.7 | 111.7 | 144.7 | 110.2 | 109.7 | 109.7 |
| *** LIQUID PHASE *** | | | | | | | | | | | |
| Mole Weight | | 69.77 | 69.78 | 82.25 | | | 95.39 | 85.18 | 84.10 | 78.63 | |
| Density | lb/ft3 | 36.77 | 36.78 | 41.37 | | | 38.30 | 44.09 | 37.85 | 42.17 | |
| Therm Cond | BTU-ft/hr | 0.0524 | 0.0524 | 0.0567 | | | 0.0507 | 0.0601 | 0.0499 | 0.0645 | |
| Spec Heat | BTU/lb-F. | 0.62 | 0.62 | 0.55 | | | 0.66 | 0.51 | 0.64 | 0.51 | |
| Viscosity | lb/ft-hr | 0.33 | 0.33 | 0.51 | | | 0.38 | 0.58 | 0.36 | 0.68 | |
| Surface Tension | | 8.60 | 8.60 | 13.46 | | | 8.18 | 16.62 | 8.66 | 16.31 | |
| *** VAPOR PHASE *** | | | | | | | | | | | |
| Mole Weight | | | | | 44.91 | 32.26 | 86.64 | | | 32.26 | 64.16 |
| Density | lb/ft3 | | | | 0.78 | 0.60 | 1.31 | | | 0.60 | 1.01 |
| Therm Cond | BTU-ft/hr | | | | 0.0152 | 0.0141 | 0.0161 | | | 0.0141 | 0.0143 |
| Spec Heat | BTU/lb-F. | | | | 0.44 | 0.40 | 0.50 | | | 0.40 | 0.48 |
| Viscosity | lb/ft-hr | | | | 0.03 | 0.03 | 0.03 | | | 0.03 | 0.03 |
| Compressibility | | | | | 0.94 | 0.95 | 0.85 | | | 0.95 | 0.90 |
| Spec Heat Ratio | | | | | 1.15 | 1.23 | 1.09 | | | 1.23 | 1.11 |

In the description above, like parts are marked throughout the specification and drawings with the same reference numerals, respectively. The drawing figures are not necessarily to scale. Certain features of the invention may be shown exaggerated in scale or in somewhat schematic form and some details of conventional elements may not be shown in the interest of clarity and conciseness. The present invention is susceptible to embodiments of different forms. There are shown in the drawings, and herein are described in detail, specific embodiments of the present invention with the understanding that the present disclosure is to be considered an exemplification of the principles of the invention, and is not intended to limit the invention to that illustrated and described herein. It is to be fully recognized that the different teachings of the embodiments discussed above may be employed separately or in any suitable combination to produce desired results. Specifically, the method and system to separate oligomerization reactor effluent of the present invention may be used with any suitable oligomerization reaction wherein the oligomerization reaction products need to be separated prior to subsequent processing. In an embodiment, the method and system to separate oligomerization reactor effluent of the present invention is for separating reactor effluent of a trimerization reaction for producing 1-hexene from ethylene in the presence of a chromium based catalyst system and the detailed description above is focused on this embodiment but with the understanding that the present invention may have broader applications including the separation of products from other oligomerization reactions. Although only a few embodiments of the present invention have been described herein, it should be understood that the present invention may be embodied in many other specific forms without departing from the spirit or the scope of the present invention. Any examples included are to be considered as illustrative and not restrictive, and the invention is not to be limited to the details given herein, but may be modified within the scope of the appended claims along with their full scope of equivalents.

The invention claimed is:

1. A method of separating an oligomerization reactor effluent, comprising:
   (a) flashing the oligomerization reactor effluent into a liquid portion and a vapor portion;
   (b) feeding the liquid portion of the oligomerization reactor effluent to a liquid feed inlet on a distillation column;
   (c) feeding the vapor portion of the oligomerization reactor effluent to a vapor feed inlet on the distillation column located above the liquid feed inlet; and
   (d) withdrawing an oligomerization product stream from a side drawn outlet located between the liquid feed and vapor feed inlets.

2. The method of claim 1, wherein the oligomerization reactor effluent is from a trimerization reactor.

3. The method of claim 1, wherein the oligomerization reactor effluent is from trimerization of ethylene to 1-hexene.

4. The method of claim 3, wherein the oligomerization reactor effluent comprises a solvent.

5. The method of claim 4, wherein the solvent comprises an aliphatic solvent, an aromatic solvent, or combinations thereof, having from 3 to 9 carbon atoms.

6. The method of claim 4, wherein the solvent comprises cyclohexane, methylcyclohexane, hexane, 1-hexene, $C_7$ hydrocarbons, isobutane, propane, or mixtures of two or more thereof.

7. The method of claim 4, wherein the solvent comprises cyclohexane.

8. The method of claim 7, wherein the oligomerization reactor effluent comprises a catalyst system.

9. The method of claim 8, wherein the catalyst system comprises a chromium source, a pyrrole-containing compound, a methyl alkyl, and a halide source.

10. The method of claim 9 further comprising killing the catalyst system prior to step 1(b).

11. The method of claim 10, wherein the catalyst system is killed with an alcohol, an amine, or combinations thereof.

12. The method of claim 10, wherein the catalyst system is killed with an alcohol having eight to twelve carbon atoms per molecule.

13. The method of claim 10, wherein the catalyst system is killed with $C_8$ alcohol.

14. The method of claim 1, wherein the oligomerization product stream comprises 1-hexene and solvent.

15. The method of claim 1, wherein the oligomerization effluent is flashed by pressure reduction.

16. The method of claim 1, wherein the distilling is performed in a common distillation column.

17. The method of claim 1, further comprising a number of stages between the liquid feed inlet and the side draw outlet effective to separate heavies from the oligomerization product stream.

18. The method of claim 1, further comprising a number of stages between the vapor feed inlet and the side draw outlet effective to separate lights from the oligomerization product stream.

19. The method of claim 1, further comprising separating 1-hexene and cyclohexane from the oligomerization product stream.

20. The method of claim 1, wherein the oligomerization reactor effluent comprises:
from about 15 to about 30 wt. % 1-hexene,
from about 5 to about 15 wt. % ethylene,
from about 50 to about 80 wt. % cyclohexane,
from about 5 to about 20 wt. % lights, and
from about 0 to about 3 wt. % heavies.

21. The method of claim 1, wherein the liquid portion comprises:
from about 15 to about 30 wt. % 1-hexene,
from about 0 to about 5 wt. % ethylene,
from about 50 to about 80 wt. % cyclohexane,
from about 0 to about 5 wt. % lights, and
from about 0 to about 5 wt. % heavies.

22. The method of claim 1, wherein the vapor portion comprises:
from about 15 to about 25 wt. % 1-hexene,
from about 25 to about 50 wt. % ethylene,
from about 20 to about 40 wt. % cyclohexane,
from about 25 to about 50 wt. % lights, and
from about 0 to about 0.5 wt. % heavies.

23. The method of claim 1, wherein the oligomerization product stream comprises:
from about 15 to about 30 wt. % 1-hexene,
from about 0 to about 0.1 wt. % ethylene,
from about 70 to about 85 wt. % cyclohexane,
from about 0 to about 0.1 wt. % lights, and
from about 0 to about 1 wt. % heavies.

24. A system for separating an oligomerization reactor effluent comprising:
(a) a vapor/liquid separator to flash the oligomerization reactor effluent into a vapor portion and a liquid portion; and
(b) a distillation column in fluid communication with the vapor/liquid separator, wherein the distillation column has a side draw for withdrawing an oligomerization product stream and receives as separate feeds the vapor portion and the liquid portion from the vapor/liquid separator.

25. The system of claim 24, wherein the liquid portion is fed to the distillation column at a location below the side draw.

26. The system of claim 25, wherein the vapor portion is fed to the distillation column at a location above the side draw.

27. The system of claim 24, further comprising a trimerization reactor for providing the oligomerization reactor effluent, wherein the trimerization reactor is in fluid communication with the vapor/liquid separator.

28. The system of claim 24, wherein the vapor/liquid separator is positioned at an elevation higher than the liquid feed on the distillation column to create a hydrostatic head for flow into the distillation column.

29. The system of claim 24, further comprising a second distillation column in fluid communication with the side draw of the first distillation column, wherein the second distillation column separates trimerization product from solvent.

30. The system of claim 24, wherein the distillation column has at least 3 off-takes and at least 2 inputs.

* * * * *

UNITED STATES PATENT AND TRADEMARK OFFICE
CERTIFICATE OF CORRECTION

PATENT NO.         : 7,476,775 B2
APPLICATION NO.    : 10/792108
DATED              : January 13, 2009
INVENTOR(S)        : Bruce E. Kreischer Page 1 of 1

It is certified that error appears in the above-identified patent and that said Letters Patent is hereby corrected as shown below:

In Column 11, Line 5, replace "methyl" with --metal--

In Column 11, Line 18, insert --reactor-- before "effluent"

Signed and Sealed this

Thirty-first Day of March, 2009

JOHN DOLL
*Acting Director of the United States Patent and Trademark Office*